(12) United States Patent
Gourlaouen et al.

(10) Patent No.: US 7,736,631 B2
(45) Date of Patent: *Jun. 15, 2010

(54) COSMETIC DYE COMPOSITION WITH A LIGHTENING EFFECT FOR HUMAN KERATIN MATERIALS, COMPRISING AT LEAST ONE FLUORESCENT DYE AND AT LEAST ONE AMINOSILICONE, AND PROCESS OF DYEING

(75) Inventors: Luc Gourlaouen, Asnieres (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 1717 days.

This patent is subject to a terminal disclaimer.

(21) Appl. No.: 10/814,428

(22) Filed: Apr. 1, 2004

(65) Prior Publication Data

US 2005/0031563 A1 Feb. 10, 2005
US 2006/0078517 A9 Apr. 13, 2006

Related U.S. Application Data

(60) Provisional application No. 60/468,107, filed on May 6, 2003.

(30) Foreign Application Priority Data

Apr. 1, 2003 (FR) .................................. 03 04027

(51) Int. Cl.
  A61Q 5/08 (2006.01)
  A61Q 5/10 (2006.01)
  A61Q 19/02 (2006.01)
(52) U.S. Cl. .................... 424/62; 8/405; 8/406; 8/407; 8/408; 8/409; 8/552; 8/581; 8/602; 8/648; 132/202; 132/208
(58) Field of Classification Search .................. None
  See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Ditmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,781,354 A | 2/1957 | Mannheimer | |
| 2,798,053 A | 7/1957 | Brown | |
| 2,851,424 A | 9/1958 | Switzer et al. | |
| 2,923,692 A | 2/1960 | Ackerman et al. | |
| 2,961,347 A | 11/1960 | Floyd | |
| 2,979,465 A | 4/1961 | Parran et al. | |
| 3,014,041 A | 12/1961 | Hausermann et al. | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,639,127 A | 2/1972 | Brooker et al. | |
| 3,658,985 A | 4/1972 | Olson, Jr. et al. | |
| 3,856,550 A | 12/1974 | Bens et al. | |
| 3,874,870 A | 4/1975 | Green et al. | |
| 3,894,837 A * | 7/1975 | Kalopissis et al. ............. 8/421 |
| 3,910,862 A | 10/1975 | Barabas et al. | |
| 3,912,808 A | 10/1975 | Sokol | |
| 3,915,921 A | 10/1975 | Schlatzer, Jr. | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |

(Continued)

FOREIGN PATENT DOCUMENTS

AT 302 534 10/1972

(Continued)

OTHER PUBLICATIONS

International Cosmetic Ingredient Dictionary and Handbook, Seventh Edition, p. 73 (1997).*
English language Derwent Abstract of JP 2001-302473.
English language Derwent Abstract of JP 2002-326911.
English language Derwent Abstract of JP 9-183714.
Mishra, J.K. et al. "Synthesis of some bischromophoric dyes containing nonabsorbing flexible bridge," Indian Journal of Chemistry, vol. 31B, pp. 118-112, Feb. 1992.
Office Action mailed Apr. 6, 2006 in co-pending U.S. Appl. No. 10/742,995.
Office Action mailed Aug. 24, 2006 in co-pending U.S. Appl. No. 10/814,305.

(Continued)

*Primary Examiner*—Sharmila Gollamudi Landau
*Assistant Examiner*—Barbara Frazier
(74) *Attorney, Agent, or Firm*—Finnegan, Henderson, Farabow, Garrett & Dunner

(57) ABSTRACT

The present disclosure relates to a cosmetic composition comprising at least one fluorescent dye and at least one aminosilicone; processes using this cosmetic composition and a kit comprising at least one composition comprising at least one fluorescent dye and at least one aminosilicone, which can be used to dye with a lightening effect human keratin materials for example, artificially dyed or pigmented hair, and dark skin.

13 Claims, No Drawings

U.S. PATENT DOCUMENTS

| | | | |
|---|---|---|---|
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,240,450 A | 12/1980 | Grollier et al. | |
| 4,256,458 A * | 3/1981 | Degen et al. | 8/506 |
| 4,277,581 A | 7/1981 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,509,949 A | 4/1985 | Huang et al. | |
| 4,517,174 A | 5/1985 | Jacquet et al. | |
| 4,591,610 A | 5/1986 | Grollier | |
| 4,608,250 A | 8/1986 | Jacquet et al. | |
| 4,608,379 A | 8/1986 | Boyle | |
| 4,693,935 A | 9/1987 | Mazurek | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,781,724 A | 11/1988 | Wajaroff et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,961,925 A | 10/1990 | Tsujino et al. | |
| 4,972,037 A | 11/1990 | Garbe et al. | |
| 4,996,059 A | 2/1991 | Grollier et al. | |
| 4,997,745 A | 3/1991 | Kawamura et al. | |
| 5,009,880 A | 4/1991 | Grollier et al. | |
| 5,057,311 A | 10/1991 | Hanazawa et al. | |
| 5,089,252 A | 2/1992 | Grollier et al. | |
| 5,089,578 A | 2/1992 | Valint et al. | |
| 5,139,037 A | 8/1992 | Grollier et al. | |
| 5,188,639 A | 2/1993 | Schultz et al. | |
| 5,196,189 A | 3/1993 | Jacquet et al. | |
| 5,275,808 A | 1/1994 | De Groot et al. | |
| 5,316,551 A | 5/1994 | Wenke | |
| 5,356,438 A | 10/1994 | Kim et al. | |
| 5,445,655 A | 8/1995 | Kuhn et al. | |
| 5,635,461 A | 6/1997 | Onitsuka et al. | |
| 5,708,151 A | 1/1998 | Möckli | |
| 5,733,343 A | 3/1998 | Mockli | |
| 5,744,127 A | 4/1998 | Giuseppe et al. | |
| 5,792,221 A | 8/1998 | Lagrange et al. | |
| 5,830,446 A | 11/1998 | Berthiaume et al. | |
| 5,833,997 A | 11/1998 | Mahieu et al. | |
| 5,853,708 A | 12/1998 | Cauwet et al. | |
| 5,873,494 A | 2/1999 | Dallas, Jr. | |
| 5,914,373 A | 6/1999 | Glancy et al. | |
| 5,958,392 A | 9/1999 | Grollier et al. | |
| 5,961,667 A | 10/1999 | Doehling et al. | |
| 5,962,522 A | 10/1999 | Wacher et al. | |
| 5,990,479 A | 11/1999 | Weiss et al. | |
| 6,001,135 A | 12/1999 | Rondeau et al. | |
| 6,089,251 A | 7/2000 | Pestel | |
| 6,106,577 A | 8/2000 | Audousset et al. | |
| 6,120,780 A | 9/2000 | Dupuis et al. | |
| 6,156,077 A | 12/2000 | Shibata et al. | |
| 6,180,666 B1 | 1/2001 | Wacher et al. | |
| 6,225,198 B1 | 5/2001 | Alivisatos et al. | |
| 6,260,556 B1 | 7/2001 | Legrand et al. | |
| 6,375,939 B1 | 4/2002 | Dubief et al. | |
| 6,375,958 B1 | 4/2002 | Cauwet et al. | |
| 6,391,062 B1 | 5/2002 | Vandenbossche et al. | |
| 6,436,151 B2 | 8/2002 | Cottard et al. | |
| 6,436,153 B2 | 8/2002 | Rondeau | |
| 6,451,068 B1 * | 9/2002 | Genet et al. | 8/405 |
| 6,475,248 B2 | 11/2002 | Ohashi et al. | |
| 6,570,019 B2 | 5/2003 | Pasquier et al. | |
| 6,576,024 B1 | 6/2003 | Lang et al. | |
| 6,592,630 B2 | 7/2003 | Matsunaga et al. | |
| 6,616,709 B2 | 9/2003 | Ohashi et al. | |
| 6,712,861 B2 | 3/2004 | Rondeau | |
| 6,770,102 B1 | 8/2004 | Moeller et al. | |
| 6,822,039 B1 | 11/2004 | Monfreux-Gaillard et al. | |
| 7,147,673 B2 * | 12/2006 | Plos et al. | 8/405 |
| 7,150,764 B2 * | 12/2006 | Plos et al. | 8/405 |
| 7,186,278 B2 * | 3/2007 | Plos et al. | 8/405 |
| 7,192,454 B2 * | 3/2007 | Plos et al. | 8/405 |
| 7,195,651 B2 * | 3/2007 | Plos et al. | 8/405 |
| 7,198,650 B2 * | 4/2007 | Pourille-Grethen et al. | 8/405 |
| 7,204,860 B2 * | 4/2007 | Plos et al. | 8/405 |
| 7,208,018 B2 * | 4/2007 | Gourlaouen et al. | 8/405 |
| 7,250,064 B2 * | 7/2007 | Plos et al. | 8/405 |
| 7,303,589 B2 * | 12/2007 | Greaves et al. | 8/405 |
| 2001/0010812 A1 | 8/2001 | Chevalier et al. | |
| 2001/0023514 A1 | 9/2001 | Cottard et al. | |
| 2001/0023515 A1 | 9/2001 | Cottard et al. | |
| 2001/0031270 A1 | 10/2001 | Douin et al. | |
| 2001/0034914 A1 | 11/2001 | Saunier et al. | |
| 2001/0054206 A1 * | 12/2001 | Matsunaga et al. | 8/405 |
| 2001/0055580 A1 | 12/2001 | Belli et al. | |
| 2002/0004956 A1 | 1/2002 | Rondeau | |
| 2002/0012681 A1 | 1/2002 | George et al. | |
| 2002/0026676 A1 | 3/2002 | Ohashi et al. | |
| 2002/0034489 A1 | 3/2002 | Wiegland et al. | |
| 2002/0046431 A1 | 4/2002 | Laurent et al. | |
| 2002/0046432 A1 | 4/2002 | Rondeau | |
| 2002/0088063 A1 | 7/2002 | Ohashi et al. | |
| 2002/0131941 A1 | 9/2002 | Habeck et al. | |
| 2002/0176836 A9 | 11/2002 | Belli et al. | |
| 2002/0176875 A9 | 11/2002 | Douin et al. | |
| 2003/0000023 A9 | 1/2003 | Rondeau | |
| 2003/0019052 A1 | 1/2003 | Pratt | |
| 2003/0019053 A9 | 1/2003 | Rondeau | |
| 2003/0055268 A1 | 3/2003 | Pasquier et al. | |
| 2003/0074747 A1 | 4/2003 | Vuarier et al. | |
| 2003/0124079 A1 | 7/2003 | Mougin et al. | |
| 2003/0131424 A1 | 7/2003 | Audousset et al. | |
| 2004/0019981 A1 | 2/2004 | Cottard et al. | |
| 2004/0034945 A1 | 2/2004 | Javet et al. | |
| 2004/0037796 A1 | 2/2004 | Cottard et al. | |
| 2004/0049860 A1 | 3/2004 | Cottard et al. | |
| 2004/0105830 A1 | 6/2004 | Boswell et al. | |
| 2004/0141943 A1 | 7/2004 | Mougin et al. | |
| 2004/0148711 A1 | 8/2004 | Rondeau | |
| 2004/0205901 A1 | 10/2004 | Cottard et al. | |
| 2004/0258641 A1 | 12/2004 | Plos et al. | |
| 2005/0005368 A1 | 1/2005 | Plos et al. | |
| 2005/0005369 A1 | 1/2005 | Plos et al. | |
| 2005/0008593 A1 | 1/2005 | Plos et al. | |
| 2005/0028301 A1 | 2/2005 | Pastore | |
| 2005/0144741 A1 | 7/2005 | Lang et al. | |

FOREIGN PATENT DOCUMENTS

| | | |
|---|---|---|
| CA | 1255603 | 6/1989 |
| CH | 487 231 | 3/1970 |
| DE | 33 133 32 | 10/1994 |
| DE | 196 46 804 A1 | 5/1997 |
| DE | 196 28 357 A1 | 1/1998 |
| DE | 199 23 438 A1 | 11/2000 |
| DE | 199 26 377 A1 | 12/2000 |
| DE | 199 36 911 A1 | 2/2001 |
| DE | 199 62 348 A1 | 7/2001 |
| DE | 100 29 441 A1 | 1/2002 |

| | | | | | | |
|---|---|---|---|---|---|---|
| DE | 101 17 336 A1 | 10/2002 | | JP | 2-200612 | 8/1990 |
| DE | 101 41 683 A1 | 6/2003 | | JP | 6-128128 | 5/1994 |
| DE | 101 48 844 A1 | 10/2003 | | JP | 6-183935 | 7/1994 |
| EP | 0 087 060 B1 | 8/1983 | | JP | 6-227954 | 8/1994 |
| EP | 0 095 238 A2 | 11/1983 | | JP | 8-183716 | 7/1996 |
| EP | 0 080 976 B1 | 9/1986 | | JP | 8-208448 | 8/1996 |
| EP | 0 173 109 | 10/1989 | | JP | 8-259426 | 10/1996 |
| EP | 0 370 470 B1 | 5/1990 | | JP | 9-183714 | 7/1997 |
| EP | 370470 * | 5/1990 | | JP | 10-23629 | 9/1998 |
| EP | 0 412 704 B1 | 2/1991 | | JP | 11-021214 | 1/1999 |
| EP | 0 412 707 B1 | 2/1991 | | JP | 11-60453 | 3/1999 |
| EP | 0 445 342 B1 | 9/1991 | | JP | 11-343218 | 12/1999 |
| EP | 0 486 135 B1 | 5/1992 | | JP | 2000-01417 | 1/2000 |
| EP | 0 122 324 B2 | 2/1993 | | JP | 2000-86472 | 3/2000 |
| EP | 0 337 354 B1 | 2/1994 | | JP | 2000-505841 | 5/2000 |
| EP | 0 582 152 B1 | 2/1994 | | JP | 2001-172120 | 6/2001 |
| EP | 0 395 282 | 3/1995 | | JP | 2001-220330 | 8/2001 |
| EP | 0 503 853 | 5/1996 | | JP | 2001-226217 | 8/2001 |
| EP | 0 714 954 A2 | 6/1996 | | JP | 2001-261534 | 9/2001 |
| EP | 0 733 355 A2 | 9/1996 | | JP | 2001-261536 | 9/2001 |
| EP | 0 750 899 A2 | 1/1997 | | JP | 2001-294519 | 10/2001 |
| EP | 0 808 150 | 11/1997 | | JP | 2001-302473 | 10/2001 |
| EP | 0 815 828 B1 | 6/1999 | | JP | 2001-516701 | 10/2001 |
| EP | 0 970 684 A1 | 1/2000 | | JP | 2001-516705 | 10/2001 |
| EP | 1 023 891 B1 | 8/2000 | | JP | 2001-516706 | 10/2001 |
| EP | 1 099 437 | 5/2001 | | JP | 2001-516707 | 10/2001 |
| EP | 1 132 076 A1 | 9/2001 | | JP | 2002-12523 | 1/2002 |
| EP | 1 133 977 A2 | 9/2001 | | JP | 2002-12530 | 1/2002 |
| EP | 1 142 559 | 10/2001 | | JP | 2002-47151 | 2/2002 |
| EP | 1 191 041 A2 | 3/2002 | | JP | 2002-226338 | 8/2002 |
| FR | 1492597 | 9/1966 | | JP | 2002-249419 | 9/2002 |
| FR | 1583363 | 10/1969 | | JP | 2002-326911 | 11/2002 |
| FR | 2077143 | 10/1971 | | JP | 2003-55177 | 2/2003 |
| FR | 2080759 | 11/1971 | | JP | 2004-059468 | 2/2004 |
| FR | 2103210 | 7/1972 | | JP | 2004-307494 | 11/2004 |
| FR | 2162025 | 7/1973 | | JP | 2004-307495 | 11/2004 |
| FR | 2190406 | 2/1974 | | WO | WO 93/11103 | 6/1993 |
| FR | 2252840 | 6/1975 | | WO | WO 93/23009 | 11/1993 |
| FR | 2270846 | 12/1975 | | WO | WO 93/23446 | 11/1993 |
| FR | 2280 361 | 2/1976 | | WO | WO 94/02022 | 2/1994 |
| FR | 2316271 | 1/1977 | | WO | WO 95/00578 | 1/1995 |
| FR | 2320330 | 3/1977 | | WO | WO 95/01772 | 1/1995 |
| FR | 2336434 | 7/1977 | | WO | WO 95/15144 | 6/1995 |
| FR | 2368508 | 5/1978 | | WO | WO 97/18795 | 5/1997 |
| FR | 2383660 | 10/1978 | | WO | WO 99/12846 | 3/1999 |
| FR | 2393573 | 1/1979 | | WO | WO 99/13822 | 3/1999 |
| FR | 2411219 | 7/1979 | | WO | WO 99/13823 | 3/1999 |
| FR | 2416723 | 9/1979 | | WO | WO 99/13824 | 3/1999 |
| FR | 2470596 | 6/1981 | | WO | WO 99/13828 | 3/1999 |
| FR | 2505348 | 11/1982 | | WO | WO 99/13841 | 3/1999 |
| FR | 2519863 | 7/1983 | | WO | WO 99/13844 | 3/1999 |
| FR | 2542997 | 9/1984 | | WO | WO 99/13845 | 3/1999 |
| FR | 2586913 | 3/1987 | | WO | WO 99/13846 | 3/1999 |
| FR | 2589476 | 5/1987 | | WO | WO 99/13847 | 3/1999 |
| FR | 2598611 | 11/1987 | | WO | WO 99/13849 | 3/1999 |
| FR | 2692572 | 6/1992 | | WO | WO 99/20235 A1 | 4/1999 |
| FR | 2741261 | 5/1997 | | WO | WO 99/36045 | 7/1999 |
| FR | 2 773 470 | 7/1999 | | WO | WO 00/31154 A1 | 6/2000 |
| FR | 2 773 864 | 7/1999 | | WO | WO 00/46839 A2 | 8/2000 |
| FR | 2 797 877 | 3/2001 | | WO | WO 00/68282 | 11/2000 |
| FR | 2800612 | 5/2001 | | WO | WO 00/71085 A2 | 11/2000 |
| FR | 2811993 | 1/2002 | | WO | WO 01/43714 A1 | 6/2001 |
| FR | 2 816 832 A1 | 5/2002 | | WO | WO 01/62759 A1 | 8/2001 |
| FR | 2820032 | 8/2002 | | WO | WO 01/78669 | 10/2001 |
| FR | 2830189 | 4/2003 | | WO | WO 02/31060 A1 | 4/2002 |
| FR | 2 853 230 A1 | 10/2004 | | WO | WO 02/32386 A2 | 4/2002 |
| GB | 746864 | 3/1956 | | WO | WO 02/38115 A1 | 5/2002 |
| GB | 759385 | 10/1956 | | WO | WO 02/39964 A1 | 5/2002 |
| GB | 1214394 | 1/1970 | | WO | WO 02/45673 A2 | 6/2002 |
| GB | 1546809 | 5/1979 | | WO | WO 02/50224 A1 | 6/2002 |
| GB | 1554331 | 10/1979 | | WO | WO 02/058646 A1 | 8/2002 |
| JP | 48-17362 | 5/1973 | | WO | WO 02/058647 A1 | 8/2002 |
| JP | 54-86521 | 7/1979 | | WO | WO 02/074270 | 9/2002 |

| WO | WO 03/022232 A2 | 3/2003 |
| WO | WO 03/028685 A1 | 4/2003 |
| WO | WO 03/029359 | 4/2003 |

OTHER PUBLICATIONS

Office Action mailed Aug. 28, 2006 in co-pending U.S. Appl. No. 10/814,236.
Office Action mailed Aug. 28, 2006 in co-pending U.S. Appl. No. 10/814,300.
Office Action mailed Jul. 7, 2006, in co-pending U.S. Appl. No. 10/814,585.
Office Action mailed Jun. 21,2006, in co-pending U.S. Appl. No. 10/814,336.
Office Action mailed Jun. 8, 2006, in co-pending U.S. Appl. No. 10/814,430.
Office Action mailed May 26, 2006, in co-pending U.S. Appl. No. 10/490,869.
Office Action mailed May 30, 2006, in co-pending U.S. Appl. No. 10/814,338.
Office Action mailed Oct. 23, 2006 in co-pending U.S. Appl. No. 10/742,995.
CAS Abstract for JP 2000-136340—Chemical Abstracts Service; Database Accession No. 2000: 317079; XP-002269220, JP 2000136340 (Pentel Co., Ltd.), May 16, 2000.
Co-pending U.S. Appl. No. 10/814,333, filed Apr. 1, 2004.
Co-pending U.S. Appl. No. 10/814,334, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Apr. 1, 2004.
Co-pending U.S. Appl. No. 10/814,336, filed Apr. 1, 2004.
English Language Derwent Abstract of DE 33 133 32.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2 773 470.
English Language Derwent Abstract of FR 2,797,877.
English Language Derwent Abstract of FR 2,800,612.
English Language Abstract of FR 2 589 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-294519.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2004-59468.
English Language Derwent Abstract of JP 2-200612.
English Language Derwent Abstract of JP 54-086521.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 8-259426.
Office Action mailed Nov. 17, 2005 in co-pending U.S. Appl. No. 10/814,336.
Office Action mailed Nov. 3, 2005 in co-pending U.S. Appl. No. 10/490,869.
Office Action mailed Nov. 2, 2005 in co-pending U.S. Appl. No. 10/814,338.
Office Action mailed Nov. 2, 2005 in co-pending U.S. Appl. No. 10/742,995.
Office Action mailed May 18, 2006 in co-pending U.S. Appl. No. 10/814,333.
Office Action mailed Mar. 27, 2006 in co-pending U.S. Appl. No. 10/814,334.
Office Action mailed Mar. 15, 2006 in co-pending U.S. Appl. No. 10/814,305.
Office Action mailed Mar. 23, 2006 in co-pending U.S. Appl. No. 10/814,300.
Office Action mailed May 25, 2006 in co-pending U.S. Appl. No. 10/814,335.
Office Action mailed Mar. 24, 2006 in co-pending U.S. Appl. No. 10/814,236.
Office Action mailed Mar. 15, 2006 in co-pending U.S. Appl. No. 10/814,337.
Jacobi, Otto and Jacobi, Gertrud, "Investigation into the reciprocal action of cosmetics and the biosphere of the stratum corneum of the skin," Cosmetics and Toiletries, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
C. D. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci. 271:380-389 (1993).
Zviak, C., The Science of Hair Care, pp. 215 and 278 (1986).
Clausen, et al., Hair Preparations, Wiley-VCH Verlag GmbH & Co., Weinheim, 2006, pp. 1-46.
Copending U.S. Appl. No. 10/885,888, filed Jul. 8, 2004.
Copending U.S. Appl. No. 11/806,306, filed May 31, 2007.
English language Abstract of DE 101 17 336, dated Oct. 10, 2002.
English language Abstract of DE 196 28 357, dated Jan. 15, 1998.
English language Abstract of DE 199 62 348, dated Jul. 5, 2001.
English language Abstract of FR 2 816 832, dated May 24, 2002.
English language Abstract of FR 2 853 230, dated Oct. 8, 2004.
Kirk-Othmer, Encyclopedia of Chemical Technology, "Hair Preparations," 4th Edition, vol. 12, pp. 881-918, John Wiley & Sons: New York (1994).
Kirk-Othmer, Encyclopedia of Chemical Technology, "Hair Preparations," pp. 1-33, John Wiley & Sons: New York (2008).
Morishima, Y., "Self-Assembling Amphiphilic Ployelectrolytes and Their Nanostructures," Chinese Journal of Polymer Science, vol. 18, No. 40, 2000, pp. 323- 336.
Noda, et al., "Micelle Formation of Random Copolymers of Sodium 2-(Acrylamido)-2-methylpropanesulfonate and a Nonionic Surfactant Macromonomer in Water as Studied by Fluorescence and Dynamic Light Scattering," Macromolecules, vol. 33, No. 10, 2000, pp. 3694-3704.
Noda, et al., "Solution Properties of Micelle Networks Formed by Nonionic Surfactant Moieties Covalently Bound to a Polyelectrolyte: Salt Effects on Rheological Behavior," Langmuir, vol. 16, No. 12, 2000, pp. 5324-5332.
Noda, et al., "Stimuli-Responsive Amphiphilic Copolymers of Sodium 2-(acrylamido)-2-methylpropanesulfonate and Associative Macromonomers," Polymer Preprints, vol. 40, No. 2, 1999, pp. 220-221.
Office Action mailed Apr. 23, 2007, in co-pending U.S. Appl. No. 10/885,888.
Office Action mailed May 12, 2008, in co-pending U.S. Appl. No. 11/806,306.

Office Action mailed Oct. 11, 2007, in co-pending U.S. Appl. No. 11/806,306.

Office Action mailed Sep. 24, 2007, in co-pending U.S. Appl. No. 10/885,888.

Porter, M.R., "Nonionics," Handbook of Surfactants, 2nd Ed., Chapter 7, 1994, pp. 169-247.

Porter, M.R., Handbook of Surfactants 116-178 (Blackie & Son 1991).

Sahay, A.K. et al., "Solubilization of Surface-Active Cyanine Dyes in Cetyltrimethyl Ammonium Bromide (CTAB) Solution Through Mixed Micelle Formation," Indian Journal of Technology, vol. 27, No. 2, 1989, pp. 89-92.

STIC Search Report for U.S. Appl. No. 10/885,888, dated Apr. 10, 2007.

* cited by examiner

COSMETIC DYE COMPOSITION WITH A LIGHTENING EFFECT FOR HUMAN KERATIN MATERIALS, COMPRISING AT LEAST ONE FLUORESCENT DYE AND AT LEAST ONE AMINOSILICONE, AND PROCESS OF DYEING

This application claims benefit of U.S. Provisional Application No. 60/468,107, filed May 6, 2003.

The present disclosure relates to a composition, for example cosmetic compositions, comprising at least one fluorescent dye and at least one aminosilicone. Other aspects of the present disclosure include the processes and a device or kit for using these compositions. The present disclosure also relates to the use of compositions comprising at least one fluorescent dye and at least one aminosilicone, to dye with a lightening effect human keratin materials, for instance keratin fibers such as artificially dyed or pigmented hair, and also dark skin.

It is common for individuals who wish to lighten their skin to use cosmetic or dermatological compositions containing bleaching agents.

The substances most commonly used as bleaching agent include hydroquinone and its derivatives, kojic acid and its derivatives, azelaic acid, arbutin and its derivatives, alone or in combination with other active agents. These bleaching agents are not without drawbacks. For example, they frequently need to be used for a long time and in large amounts in order to obtain a bleaching effect on the skin. No immediate effect is observed on applying compositions comprising them. In addition, when hydroquinone and its derivatives are used in an amount that is effective to produce a visible bleaching effect, hydroquinone is known for its cytotoxicity towards melanocyte. Moreover, kojic acid and its derivatives can have the drawback of being expensive and consequently of not being able to be practicably used in large amounts in products for commercial mass distribution.

There is thus a need for cosmetic compositions that allow a lighter, uniform, homogeneous skin tone of natural appearance to be obtained, these compositions having satisfactory transparency after application to the skin.

In the field of haircare, there are mainly two major types of hair dyeing.

One type is semi-permanent dyeing, also called direct dyeing, uses dyes capable of giving the hair's natural color a moderately pronounced modification that withstands multiple shampooing. These dyes are known as direct dyes and may be used in two different ways. The colorations may be performed by applying a composition containing at least one direct dye directly to the keratin fibers, or by applying a mixture, prepared extemporaneously, of a composition containing at least one direct dye with a composition containing an oxidizing bleaching agent, which may be for example, an aqueous hydrogen peroxide solution. Such a process is then termed "lightening direct dyeing".

Another type is permanent dyeing or oxidation dyeing. This is performed with "oxidation" dye precursors, which may be colorless or weakly colored compounds which, once mixed with oxidizing products, at the time of use, can give rise to colored compounds and dyes via a process of oxidative condensation. It is often necessary to combine at least one direct dye with oxidation bases and couplers in order to neutralize or attenuate the shades with too much of a red, orange or golden glint or, alternatively, to accentuate these red, orange or golden glints.

Among the available direct dyes, nitrobenzene direct dyes may not be sufficiently strong. Indoamines, quinone dyes and natural dyes can have low affinity for keratin fibers and can consequently lead to colorations that are not sufficiently fast with respect to the various treatments to which the fibers may be subjected, for example, shampooing.

In addition, there is a need to obtain a lightening effect on human keratin fibers. This lightening is conventionally obtained via a process of bleaching the melanins of the hair via an oxidizing system generally comprising hydrogen peroxide optionally combined with persalts. This bleaching system can have the drawback of degrading the keratin fibers and of impairing their cosmetic properties.

One object of the present inventors was to solve at least one of the problems mentioned above, and also to propose a composition that may have at least one of good dyeing affinity for keratin materials, such as keratin fibers, good resistance properties with respect to external agents, such as shampooing, and that also may make it possible to obtain lightening without damaging the treated material, for instance the keratin fiber.

The inventors have found, surprisingly and unexpectedly, that the use of fluorescent dyes, for instance those in the orange range, in the presence of aminosilicones, allows these objectives to be achieved.

A first aspect of the present disclosure is a composition comprising, in a cosmetically acceptable medium, at least one fluorescent dye that is soluble in the medium and at least one aminosilicone; with the proviso that the at least one fluorescent dye is not 2-[2-(4-dialkylamino)phenylethenyl]-1-alkylpyridinium wherein the alkyl radical of the pyridinium nucleus is chosen from methyl and ethyl radicals and the radical of the benzene nucleus is chosen from a methyl radical, and wherein the counterion is a halide.

A second aspect of the present disclosure relates to a process for dyeing human keratin fibers with a lightening effect, comprising the following steps:

a) a composition according to the present disclosure is applied to the fibers, and left on for a time that is sufficient to develop the desired coloration and lightening, b) the fibers are optionally rinsed, c) the fibers are optionally washed with shampoo and rinsed, d) the fibers are dried or are left to dry.

Yet another aspect of the present disclosure relates to the use of a composition comprising, in a cosmetically acceptable medium, at least one fluorescent dye that is soluble in the medium, and at least one aminosilicone, for dyeing human keratin materials with a lightening effect.

Still another aspect of the present disclosure relates to a multi-compartment device or "kit" for dyeing and lightening keratin fibers, comprising at least one compartment containing the composition according to the present disclosure, and at least one other compartment containing a composition comprising at least one oxidizing agent.

The compositions of the present disclosure, for example, may allow better fixing of the fluorescent dye onto the keratin materials, which may result in an increased fluorescent effect and a lightening effect that may be greater than that obtained with the fluorescent dye used alone. Better resistance of the resulting color with respect to washing or shampooing may also found.

Other characteristics and advantages of the present disclosure will become clear upon reading the description and the examples that follow.

Unless otherwise indicated, the limits of the ranges of values that are given in the description are included in these ranges.

As mentioned above, the composition according to the invention comprises at least one fluorescent dye. For the purposes of the present disclosure, the term "fluorescent dye" means a dye which comprises a molecule that colors by itself, and thus absorbs light in the visible spectrum and possibly in the ultraviolet spectrum, such as wavelengths ranging from about 360 to about 760 nanometres, but which, in contrast with a standard dye, converts the absorbed energy into fluorescent light of a longer wavelength emitted in the visible region of the spectrum.

A fluorescent dye as disclosed herein can be differentiated from an optical brightener. Optical brighteners, which are also known as brighteners, fluorescent brighteners, fluorescent brightening agents, fluorescent whitening agents, whiteners and fluorescent whiteners, are colorless transparent compounds, which do not dye because they do not absorb light in the visible region, but only in the ultraviolet region, i.e., wavelengths ranging from about 200 to about 400 nanometres, and convert the absorbed energy into fluorescent light of a longer wavelength emitted in the visible region of the spectrum; the color impression is then generated by purely fluorescent light that is predominantly blue, i.e. wavelengths ranging from about 400 to about 500 nanometres.

The fluorescent dye used in the composition as disclosed herein is soluble in the medium of the composition. It should be noted that the fluorescent dye differs therein from a fluorescent pigment, which itself is insoluble in the medium of the composition.

For example, the fluorescent dye used in the composition of the present disclosure, which may be optionally neutralized, is soluble in the medium of the composition to at least about 0.001 g/l, for example, at least about 0.5 g/l, such as at least about 1 g/l and, according to one aspect of the disclosure, for example, at least about 5 g/l, at a temperature ranging from about 15° C. to about 25° C.

Moreover, the composition according to the present disclosure, does not comprise, as fluorescent dye, a 2-[2-(4-dialkylamino)phenylethenyl]-1-alkylpyridinium wherein the alkyl radical of the pyridinium nucleus is chosen from methyl and ethyl radicals and the alkyl radical of the benzene nucleus is chosen from a methyl radical, and wherein the counterion is a halide.

In accordance with another aspect of the present invention, the composition does not comprise, as fluorescent dye, a compound chosen from azo, azomethine and methine monocationic heterocyclic fluorescent dyes.

For example, the fluorescent dyes according to the present disclosure may be dyes in the orange range.

For further example, the fluorescent dyes of the present disclosure may result in a reflectance maximum that is in the wavelength range from about 500 to about 650 nanometres, such as in the wavelength range from about 550 to about 620 nanometres.

Some of the fluorescent dyes according to the present invention are compounds that are known per se. As examples of fluorescent dyes that may be used, non-limiting mention may be made of: naphthalimides; cationic or non-cationic coumarins; xanthenodiquinolizines, such as, sulphorhodamines; azaxanthenes; naphtholactams; azlactones; oxazines; thiazines; dioxazines; polycationic fluorescent dyes of azo, azomethine or methine type, alone or as mixtures. For instance, the at least one fluorescent dye may be chosen from: naphthalimides; cationic and non-cationic coumarins; azaxanthenes; naphtholactams; azlactones; oxazines; thiazines; dioxazines; and polycationic fluorescent dyes chosen from azo, azomethine and methine type.

Among the fluorescent dyes listed above, non-limiting mention may be made of the following:

Brilliant Yellow B6GL sold by the company Sandoz and having the following structure:

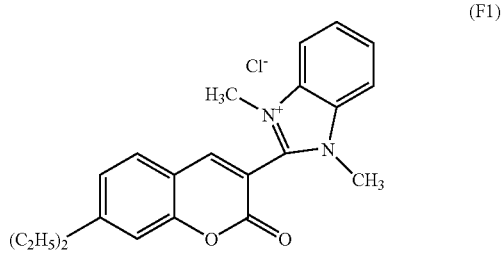

Basic Yellow 2, or Auramine O, sold by the companies Prolabo, Aldrich or Carlo Erba and having the following structure:

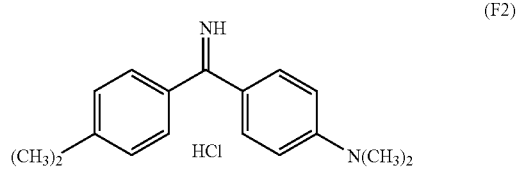

also known as 4,4'-(imidocarbonyl)bis(N,N-dimethylaniline) monohydrochloride—CAS number 2465-27-2.

Non-limiting mention may also be made of the compounds of formula (F3):

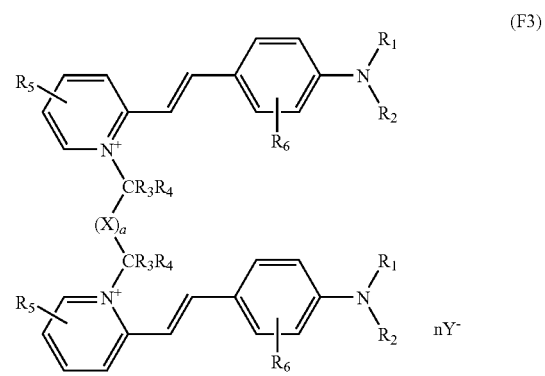

wherein:
$R_1$ and $R_2$, which may be identical or different, may be chosen from:
  hydrogen atoms;
  linear and branched alkyl radicals containing from 1 to 10 carbon atoms, such as from 1 to 4 carbon atoms, optionally interrupted with at least one entity chosen from hetero atoms and groups comprising at least one heteroatoms, and/or optionally substituted with at least one entity chosen from hetero atoms, groups comprising at least one hetero atom, and halogen atoms;
  aryl and arylalkyl radicals, wherein the aryl group comprises 6 carbon atoms and the alkyl radical comprises from 1 to 4 carbon atoms; the aryl radical may optionally be substituted with at least one linear or branched alkyl radical comprising from 1 to 4 carbon atoms, wherein the alkyl radicals may optionally be interrupted with at least one entity chosen from hetero atoms and groups comprising at least one hetero atom, and/or substituted with at least one entity chosen from hetero atoms, groups comprising at least one hetero atom, halogen atoms;

$R_1$ and $R_2$ may optionally be linked so as to form a heterocycle with the nitrogen atom and may comprise at least one hetero atoms, the heterocycle optionally being substituted with at least one linear or branched alkyl radical, for instance comprising from 1 to 4 carbon atoms and wherein the alkyl radicals may optionally be interrupted with at least one entity chosen from hetero atoms and groups comprising at least one hetero atom, and/or optionally substituted with at least one entity chosen from hetero atoms, groups comprising at least one hetero atom, and halogen atoms;

$R_1$ or $R_2$ may optionally be engaged in a heterocycle comprising the nitrogen atom and one of the carbon atoms of the phenyl group bearing the nitrogen atom;

$R_3$ and $R_4$, which may be identical or different, may be chosen from hydrogen atoms and alkyl radicals containing from 1 to 4 carbon atoms;

$R_5$, which may be identical or different, may be chosen from hydrogen atoms, halogen atoms, and linear and branched alkyl radicals containing from 1 to 4 carbon atoms, optionally interrupted with at least one hetero atom;

$R_6$, which may be identical or different, may be chosen from hydrogen atoms; halogen atoms; and linear and branched alkyl radicals containing from 1 to 4 carbon atoms, wherein the alkyl radicals may be optionally interrupted with at least one entity chosen from hetero atoms and groups bearing at least one hetero atom, and/or substituted with at least one entity chosen from hetero atoms, groups bearing at least one hetero atom, and halogen atoms;

X may be chosen from:
linear and branched alkyl radicals containing from 1 to 14 carbon atoms and alkenyl radicals containing from 2 to 14 carbon atoms, optionally interrupted with at least one entity chosen from hetero atoms and groups containing at least one hetero atom, and/or optionally substituted with at least one entity chosen from hetero atoms, groups containing at least one hetero atom, and halogen atoms;
5- and 6-membered heterocyclic radicals optionally substituted with at least one entity chosen from linear and branched alkyl radicals containing from 1 to 14 carbon atoms, optionally substituted with at least one hetero atom; linear and branched aminoalkyl radicals containing from 1 to 4 carbon atoms, optionally substituted with at least one hetero atom; and halogen atoms;
fused and non-fused aromatic and diaromatic radicals, optionally separated with an alkyl radical containing from 1 to 4 carbon atoms, wherein the aromatic and diaromatic radicals may optionally be substituted with at least one entity chosen from halogen atoms and alkyl radicals containing from 1 to 10 carbon atoms optionally substituted and/or interrupted with at least one hetero atom and/or group bearing at least one hetero atom;
dicarbonyl radicals;
the group X may possibly bear at least one cationic charge;
a is equal to 0 or 1;
$Y^-$, which may be identical or different, is chosen from organic and mineral anions;
n is an integer ranging from 2 to the number of cationic charges present in the fluorescent compound.

It should be recalled that the term "hetero atom" indicates an oxygen or nitrogen atom.

Among the groups comprising such atoms, non-limiting mention may be made of hydroxyl, alkoxy, carbonyl, amino, ammonium, amido (—N—CO—) and carboxyl (—O—CO— or —CO—O—) groups.

With respect to the alkenyl groups, they may comprise at least one unsaturated carbon-carbon bonds (—C═C—), such as only one carbon-carbon double bond.

In this general formula, the radicals $R_1$ and $R_2$, which may be identical or different, may be chosen from, for example:
hydrogen atoms;
alkyl radicals containing from 1 to 10 carbon atoms, for instance from 1 to 6 carbon atoms; such as from 1 to 4 carbon atoms, optionally interrupted with an oxygen atom or optionally substituted with at least one entity chosen from hydroxyl, amino and ammonium radicals and chlorine and fluorine atoms;
benzyl and phenyl radicals optionally substituted with an alkyl or alkoxy radical containing from 1 to 4 carbon atoms, for instance 1 to 2 carbon atoms;
forming with the nitrogen atom, a heterocyclic radical chosen from pyrrolo, pyrrolidino, imidazolino, imidazolo, imidazolium, pyrazolino, piperazino, morpholino, morpholo, pyrazolo and triazolo radicals, optionally substituted with at least one linear or branched alkyl radical containing from 1 to 4 carbon atoms, which may be optionally interrupted and/or substituted with a nitrogen and/or oxygen atom and/or group bearing a nitrogen and/or oxygen atom.

With respect to the abovementioned amino and ammonium radicals, the radicals borne by the nitrogen atom may be identical or different and may for example, be chosen from hydrogen atoms, $C_1$-$C_{10}$ for instance, $C_1$-$C_4$, alkyl radicals, and arylalkyl radicals in which, for example, the aryl radical contains 6 carbon atoms and the alkyl radical contains from 1 to 10 carbon atoms, such as from 1 to 4 carbon atoms.

According to one aspect of the present disclosure, the radicals $R_1$ and $R_2$, which may be identical or different, may be chosen from hydrogen atoms; linear and branched $C_1$-$C_6$ alkyl radicals; $C_2$-$C_6$ alkyl radicals substituted with a hydroxyl radical; $C_2$-$C_6$ alkyl radicals bearing an amino or ammonium group; $C_2$-$C_6$ chloroalkyl radicals; $C_2$-$C_6$ alkyl radicals interrupted with an entity chosen from oxygen atoms and groups bearing an oxygen atom, for example ester; aromatic radicals, for instance phenyl, benzyl and 4-methylphenyl; heterocyclic radicals such as pyrrolo, pyrrolidino, imidazolo, imidazolino, imidazolium, piperazino, morpholo, morpholino, pyrazolo and triazolo radicals, optionally substituted with at least one entity chosen from $C_1$-$C_6$ alkyl and aromatic radicals.

For further example, the radicals $R_1$ and $R_2$, which may be identical or different, may be chosen from hydrogen atoms, linear and branched $C_1$-$C_6$ alkyl radicals, such as methyl, ethyl, n-butyl and n-propyl radicals; 2-hydroxyethyls; alkyltrimethylammonium and alkyltriethylammonium radicals, the alkyl radical comprising linear $C_2$-$C_6$ alkyl radicals; (di)alkylmethylamino and (di)alkylethylamino radicals, the alkyl radical comprising linear $C_1$-$C_6$ alkyl radicals; —$CH_2CH_2Cl$; —$(CH_2)_n$—$OCH_3$ and —$(CH_2)_n$—$OCH_2CH_3$ wherein n is an integer ranging from 2 to 6; —$CH_2CH_2$—$OCOCH_3$; and —$CH_2CH_2COOCH_3$.

For instance, the radicals $R_1$ and $R_2$, which may be identical or different, may be identical, and may be chosen from methyl and ethyl radicals.

The radicals $R_1$ and $R_2$, which may be identical or different, may also be a heterocyclic radical chosen from pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo heterocyclic radicals.

The radicals $R_1$ and $R_2$, which may be identical or different, may also be linked so as to form a heterocycle of formulae (I) and (II):

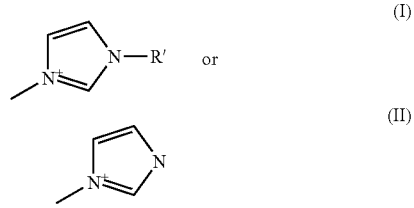

wherein R' is chosen from hydrogen atoms and $C_1$-$C_3$ alkyl radicals, —$CH_2CH_2OH$, and —$CH_2CH_2OCH_3$.

In accordance with another aspect of the present disclosure, $R_5$, which may be identical or different, may be chosen from hydrogen atoms, fluorine and chlorine atoms, and linear and branched alkyl radicals containing from 1 to 4 carbon atoms optionally interrupted with an oxygen or nitrogen atom.

It is noted that the substituent $R_5$, if it is other than hydrogen, may be in position 3 and/or 5, relative to the carbon of the ring bearing the nitrogen substituted with the radicals $R_1$ and $R_2$, for instance, in position 3 relative to that carbon.

For further example, the radicals $R_5$, which may be identical or different, may be chosen from hydrogen atoms; linear and branched $C_1$-$C_4$ alkyl radicals; —O—$R_{51}$ wherein $R_{51}$ is chosen from linear $C_1$-$C_4$ alkyl radicals; —$R_{52}$—O—$CH_3$ wherein $R_{52}$ is chosen from linear $C_2$-$C_3$ alkyl radicals; —$R_{53}$—N($R_{54}$)$_2$ wherein $R_{53}$ is chosen from linear $C_2$-$C_3$ alkyl radicals and $R_{54}$, which may be identical or different, is chosen from hydrogen atoms and methyl radicals. For instance, $R_5$, which may be identical or different, may be chosen from hydrogen atoms, methyl and methoxy radicals, such as $R_5$ may be a hydrogen atom.

According to another aspect of the present disclosure, the radicals $R_6$, which may be identical or different, may be chosen from hydrogen atoms; linear and branched $C_1$-$C_4$ alkyl radicals; —X wherein X may be chosen from chlorine, bromine and fluorine atoms; —$R_{61}$—O—$R_{62}$ wherein $R_{61}$ is chosen from linear $C_2$-$C_3$ alkyl radicals and $R_{62}$ is chosen from methyl radicals; —$R_{63}$—N($R_{64}$)$_2$ wherein $R_{63}$ is chosen from linear $C_2$-$C_3$ alkyl radicals and $R_{64}$, which may be identical or different, may be chosen from hydrogen atoms and methyl radicals; —N($R_{65}$)$_2$ wherein $R_{65}$, which may be identical or different, may be chosen from hydrogen atoms and linear $C_2$-$C_3$ alkyl radicals; —NHCOR$_{66}$ wherein $R_{66}$ may be chosen from $C_1$-$C_2$ alkyl radicals, $C_1$-$C_2$ chloroalkyl radicals; and —$R_{67}$—$NH_2$, —$R_{67}$—NH($CH_3$), —$R_{67}$—N($CH_3$)$_2$, —$R_{67}$—N$^+$($CH_3$)$_3$, and —$R_{67}$—N$^+$($CH_2CH_3$)$_3$ radicals wherein $R_{67}$ is chosen from $C_1$-$C_2$ alkyl radicals.

It is noted that the substituent $R_6$, if it is other than hydrogen, may be in position 2 and/or 4 relative to the nitrogen atom of the pyridinium ring, for instance in position 4 relative to the nitrogen atom.

For further example, the radicals $R_6$, which may be identical or different, may be chosen from hydrogen atoms, and methyl and ethyl radicals; for instance, $R_6$ may be a hydrogen atom.

With respect to the radicals $R_3$ and $R_4$, these radicals, which may be identical or different, may, for example, be chosen from hydrogen atoms and alkyl radicals containing from 1 to 4 carbon atoms, such as a methyl radical. For further example, $R_3$ and $R_4$ may each a hydrogen atom.

As disclosed herein, X may be chosen from:
 linear and branched alkyl radicals containing from 1 to 14 carbon atoms and alkenyl radicals containing from 2 to 14 carbon atoms, optionally interrupted with at least one entity chosen from hetero atoms and groups bearing at least one hetero atom, and/or substituted with at least one entity chosen from hetero atoms, groups bearing at least one hetero atom, and halogen atoms;
 5- and 6-membered heterocyclic radicals optionally substituted with at least one entity chosen from linear and branched alkyl radicals containing from 1 to 14 carbon atoms, linear and branched aminoalkyl radicals containing from 1 to 4 carbon atoms, optionally substituted with at least one hetero atom; and halogen atoms;
 fused and non-fused aromatic and diaromatic radicals, optionally separated with an alkyl radical containing from 1 to 4 carbon atoms, wherein the aromatic and diaromatic radicals may optionally be substituted with at least one entity chosen from halogen atoms and alkyl radicals containing from 1 to 10 carbon atoms optionally substituted and/or interrupted with at least one hetero atom and/or group bearing at least one hetero atom;
 dicarbonyl radicals.

In addition, it is possible for the group X to bear at least one cationic charge.

For example, X may be chosen from linear and branched alkyl radicals containing from 1 to 14 carbon atoms and alkenyl radicals containing from 2 to 14 carbon atoms, wherein the radicals may be interrupted with at least one entity chosen from oxygen and nitrogen atoms and groups bearing at least one hetero atom, and/or substituted with at least one entity chosen from oxygen atoms, nitrogen atoms, groups bearing at least one hetero atom, and fluorine and chlorine atoms.

Among the groups that X may be chosen from, non-limiting mention may be made of, for example, hydroxyl, alkoxy, for instance with a radical R of the $C_1$-$C_4$ alkyl type, amino, ammonium, amido, carbonyl and carboxyl groups such as —COO— or —O—CO—, for instance with a radical of alkyloxy type.

It should be noted that the nitrogen atom, if it is present, may be in a quaternized or non-quaternized form. In this case, the at least one other radical borne by the quaternized or non-quaternized nitrogen atom may be identical or different, and may be chosen from hydrogen atoms and $C_1$-$C_4$ alkyl radicals, such as methyl.

According to another aspect of the present disclosure, the group X may be chosen from 5- and 6-membered heterocyclic radicals chosen from imidazolo, pyrazolo, triazino and pyridino radicals, optionally substituted with at least one entity chosen from linear and branched alkyl radicals containing from 1 to 14 carbon atoms, such as from 1 to 10 carbon atoms, for instance, from 1 to 4 carbon atoms; linear and branched aminoalkyl radicals containing from 1 to 10 carbon atoms, such as from 1 to 4 carbon atoms, optionally substituted with an entity chosen from groups comprising at least one hetero atom, for instance a hydroxyl radical, and halogen atoms. For example, an amino group may be linked to the heterocycle.

In accordance with yet another aspect of the present disclosure, the group X may be chosen from aromatic radicals, for instance, containing 6 carbon atoms, and fused and non-fused diaromatic radicals, for instance containing from 10 to 12 carbon atoms, optionally separated with an alkyl radical containing from 1 to 4 carbon atoms, wherein the aromatic and diaromatic radicals may optionally be substituted with at least one entity chosen from halogen atoms and alkyl radicals containing from 1 to 10 carbon atoms, such as from 1 to 4 carbon atoms, and may be optionally interrupted with at least one oxygen and/or nitrogen atom and/or a group comprising at least one hetero atom, for instance carbonyl, carboxyl, amido, amino and ammonium radicals.

It should be noted that the aromatic radical, such as phenyl radicals, may be linked to the groups $CR_3R_4$ via bonds in positions 1,2; 1,3 or 1,4, such as in positions 1,3 and 1,4. If the phenyl radical linked via bonds in positions 1,4 bears at least one substituent, this substituent may be located for example, in position 1,4 relative to one of the groups $CR_3R_4$. If a phenyl radical linked via bonds in positions 1,3 bears at least one substituent, this substituent may be for example, located in position 1 and/or 3 relative to one of the groups $CR_3R_4$. In the case where X is diaromatic, it may be, for example, non-fused and comprise two phenyl radicals possibly separated with a single bond, i.e., a carbon of each of the two rings, or with an alkyl radical, such as of the $CH_2$ or $C(CH_3)_2$ type. For example, the aromatic radicals do not have to bear a substituent. It should be noted that the diaromatic radical may be linked to the groups $CR_3R_4$ via bonds in positions 4,4'.

As examples of groups X that may be used according to the present disclosure, non-limiting mention may be made of linear and branched alkyl radicals containing from 1 to 13 carbon atoms, such as methylene, ethylene, propylene, isopropylene, n-butylene, pentylene and hexylene; 2-hydroxypropylene and 2-hydroxy-n-butylene; $C_1$-$C_{13}$ alkylene radicals substituted or interrupted with at least one nitrogen and/or oxygen atoms, and/or groups bearing at least one hetero atom, for example hydroxyl, amino, ammonium, carbonyl and carboxyl groups, such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+(CH_3)_2$—$CH_2CH_2$—, CO—CO—, 3,3-dimethylpentylene, 2-acetoxyethylene, butylene-1,2,3,4-tetraol; and —CH=CH—; aromatic and diaromatic radicals substituted with at least one entity chosen from alkyl radicals, groups bearing at least one hetero atom, and halogen atoms, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; and radicals of heterocyclic type such as pyridine, and derivatives such as 2,6-bispyridine, imidazole, imidazolium and triazine.

According to one aspect of the present disclosure, X may be chosen from linear and branched $C_1$-$C_{13}$ alkyl radicals; —$CH_2CH(OH)CH_2$— groups; —$CH_2CH(Cl)CH_2$— groups; —$CH_2CH_2$—$OCOCH_2$— groups; —$CH_2CH_2COOCH_2$— groups; —Ra—O—Rb— wherein Ra is chosen from linear $C_2$-$C_6$ alkyl radicals and Rb is chosen from linear $C_1$-$C_2$ alkyl radicals; —Rc-N(Rd)-Re— wherein Rc is chosen from $C_2$-$C_9$ alkyl radicals, Rd is chosen from hydrogen atoms and $C_1$-$C_2$ alkyl radicals and Re is chosen from $C_1$-$C_6$ alkyl radicals; —Rf—$N^+(Rg)_2$-Rh— wherein Rf is chosen from linear $C_2$-$C_9$ alkyl radicals, Rg, which may be identical, are chosen from $C_1$-$C_2$ alkyl radicals and Rh is a linear $C_1$-$C_6$ alkyl radical; and —CO—CO— groups.

X may further be chosen from imidazole radicals, optionally substituted with at least one alkyl radical comprising from 1 to 14 carbon atoms, for instance from 1 to 10 carbon atoms, such as from 1 to 4 carbon atoms, for example the divalent radicals having of formula (III):

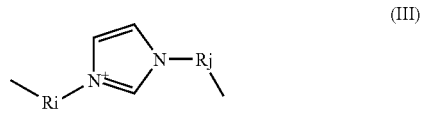

wherein Ri and Rj, which may be identical or different, are chosen from linear $C_1$-$C_6$ alkyl radicals;

X may similarly be chosen from the divalent triazine-based radicals below:

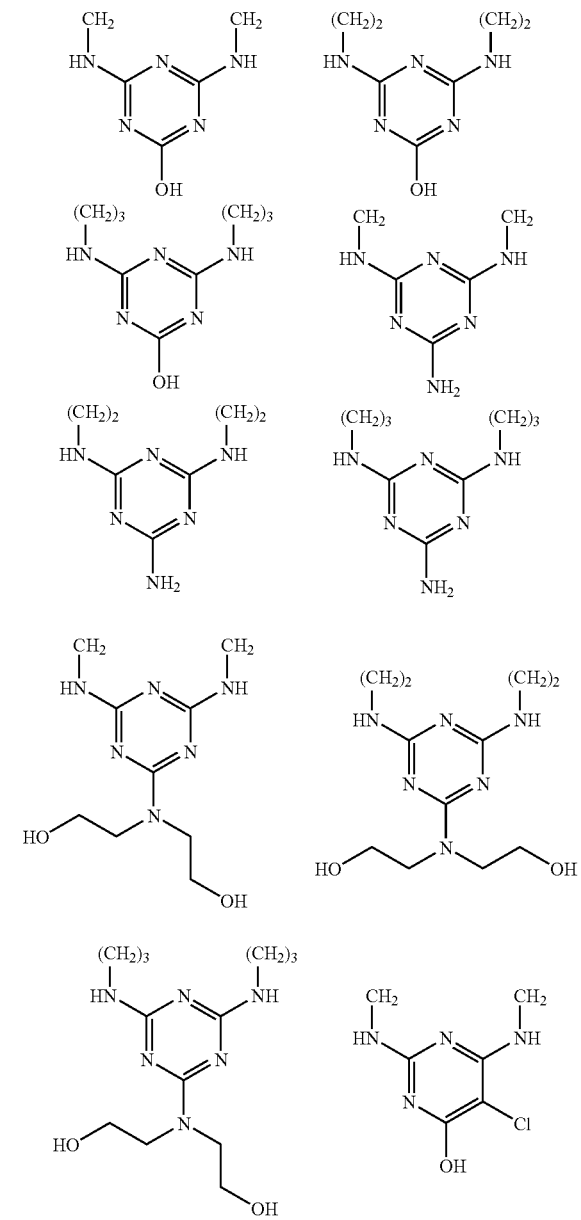

According to still another aspect of the present disclosure, X may be also chosen from the divalent aromatic radicals below:

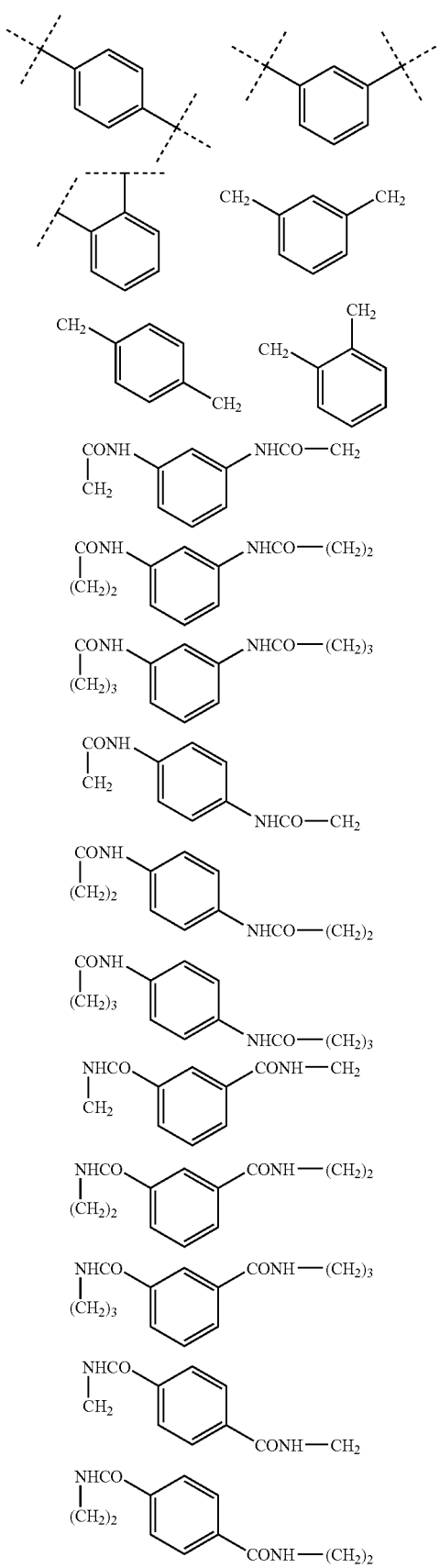

-continued

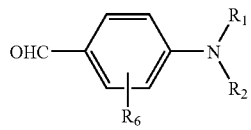

In the general formula of these fluorescent dye compounds, $Y^-$ may be chosen from organic and mineral anion. If there are several anions $Y^-$, these anions may be identical or different.

Among the anions of mineral origin that may be mentioned, without wishing to be limited thereto, are anions derived from halogen atoms, such as chlorides, iodides, sulphates, bisulphates, nitrates, phosphates, hydrogen phosphates, dihydrogen phosphates, carbonates and bicarbonates.

Among the anions of organic origin, non-limiting mention may be made of anions derived from the salts of saturated and unsaturated, aromatic and non-aromatic monocarboxylic, polycarboxylic, sulphonic, and sulphuric acids, optionally substituted with at least one entity chosen from hydroxyl and amino radicals, and halogen atoms. Non-limiting examples that are suitable for use also include acetates, hydroxyacetates, aminoacetates, (tri)chloroacetates, benzoxyacetates, propionates and derivatives bearing a chlorine atom, fumarates, oxalates, acrylates, malonates, succinates, lactates, tartrates, glycolates, citrates, benzoates and derivatives bearing a radical chosen from methyl and amino radicals, alkyl sulphates, tosylates, benzenesulphonates, toluenesulphonates, etc.

For example, the anions Y, which may be identical or different, may be chosen from chloride, sulphate, methosulphate and ethosulphate.

Finally, the integer n ranges from 2 to the number of cationic charges present in the fluorescent dye.

For further example, the fluorescent dye compounds described herein in detail may be symmetrical compounds. The fluorescent dye compounds may be synthesized by reacting, in a first step, α-picoline with a reagent comprising two leaving groups that may be chosen from halogen atoms, such as bromine and optionally chlorine, and tolylsulphonyl and methanesulphonyl groups. This first step may take place in the presence of a solvent, although this is not obligatory, for instance dimethylformamide. The number of moles of α-picoline may generally range from about 2 moles of α-picoline per mole of reagent comprising the leaving groups. In addition, the reaction may be performed at the reflux temperature of the reagent and/or of the solvent if a solvent is present.

The product derived from this first step is then placed in contact with a corresponding aldehyde having of the formula:

$$OHC-\underset{R_6}{\underset{|}{\bigcirc}}-N\underset{R_2}{\overset{R_1}{\diagdown}}$$

wherein $R_1$, $R_2$ and $R_6$ have the same meanings as described above. In this case also, the reaction may be performed in the presence of a suitable solvent, which may be for example, at reflux. The radicals $R_1$ and $R_2$ of the aldehyde may have the meaning indicated in the general formula detailed above.

It is also possible to use an aldehyde for which the radicals comprise hydrogen atoms and to perform, in accordance with standard methods, the substitution of these hydrogen atoms with suitable radicals as disclosed herein in the general formula above, once the second step is complete. Reference may be made for example, to syntheses as described in U.S. Pat. No. 4,256,458.

The at least one fluorescent dye according to the present disclosure may be present, for example, in an amount ranging from about 0.01% to about 20% by weight, for instance, from about 0.05% to about 10% by weight, such as from about 0.1% to about 5% by weight, relative to the total weight of the composition.

The composition according to the present disclosure also comprises at least one aminosilicone.

It is generally accepted in the art that the term "silicone" is intended to denote any organosilicon polymer or oligomer of linear or cyclic, branched or crosslinked structure, of variable molecular weight, obtained by polymerization and/or polycondensation of suitably functionalized silanes, and generally comprising a repetition of main units wherein the silicon atoms are linked together via oxygen atoms, such as a siloxane bond —Si—O—Si—, and optionally substituted with hydrocarbon-based radicals, which may be linked directly via a carbon atom to the silicon atoms. The hydrocarbon-based radicals that may be used, for example, include alkyl radicals, for instance ranging from $C_1$-$C_{10}$, such as methyl, fluoroalkyl radicals wherein the alkyl portion ranges from $C_1$-$C_{10}$, and aryl radicals, such as phenyl. For example, the term "aminosilicone" means any silicone comprising at least one primary, secondary or tertiary amine or a quaternary ammonium group. Also, as disclosed herein, the term "polyoxyalkylenated silicone" means any silicone comprising at least one oxyalkylenated group of $(-C_xH_{2x}O-)_a$ type wherein x ranges from 2 to 6, and wherein a is greater than or equal to 2.

In accordance with the present disclosure, the aminosilicones may be chosen from:

(a) compounds of formula (A):

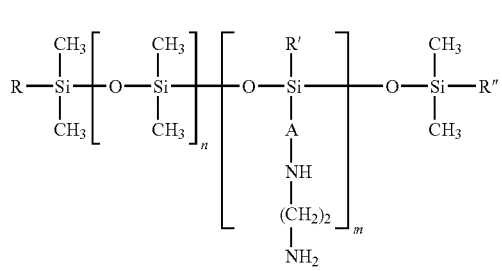

wherein R, R' and R", which may be identical or different, may be chosen from $C_1$-$C_4$ alkyl radicals, for instance $CH_3$; $C_1$-$C_4$ alkoxy radicals, for instance methoxy; and OH; A may be chosen from linear and branched $C_3$-$C_8$, such as $C_3$-$C_8$, alkylene radicals; m and n are integers that are dependent on the molecular weight, and wherein the sum of m and n ranges from 1 to 2000.

According to one aspect of the present disclosure, R, which may be identical or different, may be chosen from $C_1$-$C_4$ alkyls and hydroxyl radicals, A is chosen from $C_3$ alkylene radicals, and m and n are such that the weight-average molecular mass of the compound ranges from about 5000 to about 500 000. Some compounds of this type are referred to in the CTFA dictionary as "amodimethicone".

According to another aspect of the present disclosure, R, R' and R", which may be identical or different, are chosen from $C_1$-$C_4$ alkoxy and hydroxyl radicals, wherein at least one of the radicals R or R" is an alkoxy radical, and A Is chosen from $C_3$ alkylene radicals. The hydroxy/alkoxy molar ratio is may range, for example, from about 0.2/1 to about 0.4/1, and for instance, may be equal to 0.3. Moreover, m and n are such that the weight-average molecular mass of the compound ranges from 2000 to $10^6$. For example, n may range from 0 to 999 and m may range from 1 to 1000, wherein the sum of n and m may range from 1 to 1000. In this category of compound, non-limiting mention may be made, inter alia, of the product Belsil® ADM 652 sold by Wacker.

According to still another aspect of the present disclosure, R and R", which are different, may be chosen from $C_1$-$C_4$ alkoxy and hydroxyl radicals, wherein at least one of the radicals R and R" is an alkoxy radical, R' is chosen from methyl radicals and A are chosen from $C_3$ alkylene radicals. The hydroxy/alkoxy molar ratio may, for example, range from 1/0.8 to 1/1.1, and for instance, may be equal to 1/0.95. Moreover, m and n may be such that the weight-average molecular mass of the compound ranges from 2000 to 200 000. For instance, n may range from 0 to 999 and m may range from 1 to 1000, wherein the sum of n and m may range from 1 to 1000. Non-limiting mention may be made for example, of the product Fluid WR® 1300 sold by Wacker.

According to yet another aspect of the present disclosure, R and R" comprise hydroxyl radicals, R' is chosen from methyl radicals and A is chosen from $C_4$-$C_8$, such as $C_4$, alkylene radicals. Moreover, m and n may be such that the weight-average molecular mass of the compound ranges from 2000 to $10^6$. For example, n may range from 0 to 1999 and m may range from 1 to 2000, wherein the sum of n and m may range from 1 to 2000.

A product of this type is sold, for example, by the company Wacker under the name DC28299 from Dow Corning.

It is noted that the molecular masses of these silicones are determined by gel permeation chromatography at room temperature, polystyrene standard; styragem μ columns; THF eluent; flow rate of 1 mm/minute; wherein 200 μl of a 0.5% by weight solution of silicone in THF are injected and detection is performed by refractometry and UV-metry). For example, the aminosilicone is not chosen among the amodimethicones.

(b) the compounds corresponding to formula (B):

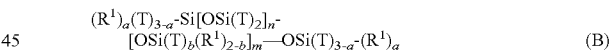

wherein:

T is chosen from hydrogen atoms and phenyl, hydroxyl, and $C_1$-$C_8$ alkyl radicals, such as methyl, a is an integer ranging from 0 to 3, for instance, 0, b ranges from 0 to 1, for instance, 1, m and n are numbers chosen such that the sum (n+m) may range, for example, from 1 to 2000, for instance, from 50 to 150, n may range from 0 to 1999, such as from 49 to 149, and m may range from 1 to 2000, such as from 1 to 10;

$R^1$ is chosen from monovalent radicals of formula $-C_qH_{2q}L$ wherein q is a number ranging from 2 to 8 and L is chosen from optionally quaternized amino groups chosen from the groups:

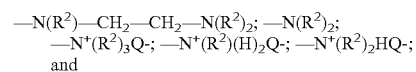
and

wherein $R^2$ may be chosen from hydrogen atoms, and phenyl, benzyl and monovalent saturated hydrocarbon-based radicals, for example C1-C20 alkyl radicals, and Q⁻ is a halide ion, for instance fluoride, chloride, bromide and iodide.

A product corresponding to this definition is the polymer named in the CTFA dictionary "trimethylsilylamodimethicone", of formula (C):

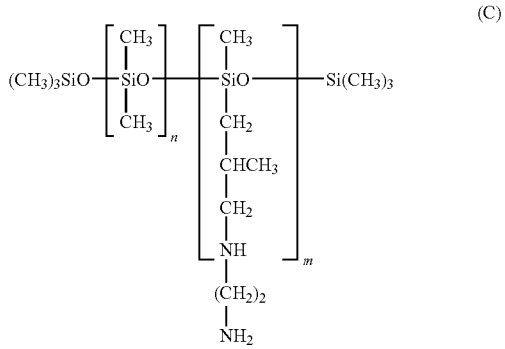

wherein n and m are chosen such that the sum (n+m) may range, for example, from 1 to 2000, for instance, from 50 to 150, n may range from 0 to 1999, such as from 49 to 149, and m may range from 1 to 2000, such as from 1 to 10.

Such compounds are described, for example, in EP 95,238; and a compound of formula (C) is sold, for example, under the name Q2-8220 by the company OSI.

(c) the compounds of formula (D):

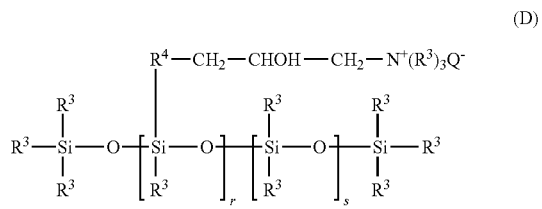

wherein:

R³ is chosen from monovalent $C_1$-$C_{18}$ hydrocarbon-based radicals, for instance, $C_1$-$C_{18}$ alkyl and $C_2$-$C_{18}$ alkenyl radicals, for example methyl;

R⁴ is chosen from divalent hydrocarbon-based radicals, for instance $C_1$-$C_{18}$ alkylene radicals and $C_1$-$C_{18}$, for example $C_1$-$C_8$, divalent alkyleneoxy radicals;

Q⁻ is a halide ion, such as chloride;

r is a mean statistical value ranging from 2 to 20, for instance, from 2 to 8;

s is a mean statistical value ranging from 20 to 200, for instance, from 20 to 50. Such compounds are described for example, in U.S. Pat. No. 4,185,087. An example of a compound falling within this category is the product sold by the company Union Carbide under the name "Ucar Silicone ALE 56".

In one aspect of the present disclosure, these compounds may be used with cationic and/or nonionic surfactants. By way of non-limiting example, the product sold under the name "Cationic Emulsion DC 929" by the company Dow Corning may be used, which comprises, besides amodimethicone, a cationic surfactant comprising a mixture of products of the formula:

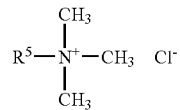

wherein R⁵ is chosen from $C_{14}$-$C_{22}$ alkenyl and alkyl radicals derived from tallow fatty acids, known under the CTFA name "tallowtrimonium chloride,"

in combination with a nonionic surfactant of formula:

$C_9H_{19}$—$C_6H_4$—$(OC_2H_4)_{10}$—OH, known under the CTFA name "Nonoxynol 10."

It is also possible to use, for example, the product sold under the name "Cationic Emulsion DC 939" by the company Dow Corning, which comprises, besides amodimethicone, a cationic surfactant, namely trimethylcetylammonium chloride, and a nonionic surfactant of formula: $C_{13}H_{27}$—$(OC_2H_4)_{12}$—OH, known under the CTFA name "trideceth-12."

Another commercial product that may be used according to the present disclosure is the product sold under the name "Dow Corning Q2 7224" by the company Dow Corning, comprising, in combination, the trimethylsilylamodimethicone of formula (C) described above, a nonionic surfactant of formula: $C_8H_{17}$—$C_6H_4$—$(OCH_2CH_2)_{40}$—OH, known under the CTFA name "octoxynol-40," a second nonionic surfactant of formula: $C_{12}H_{25}$—$(OCH_2$—$CH_2)_6$—OH, known under the CTFA name "isolaureth-6," and propylene glycol.

In the composition as disclosed herein, the aminosilicone may be present, for example, in an amount ranging from about 0.01% to about 20% by weight, relative to the weight of the composition, for example, from about 0.1% to about 10% by weight, relative to the weight of the composition.

The cosmetically acceptable medium generally consists of water or of a mixture of water and at least one common organic solvents. Among the solvents that are suitable for use, non-limiting mention may be made, for example, of alcohols such as ethyl alcohol, isopropyl alcohol, benzyl alcohol and phenylethyl alcohol, or glycols or glycol ethers, for instance ethylene glycol monomethyl ether, monoethyl ether or monobutyl ether, propylene glycol and ethers thereof, for instance propylene glycol monomethyl ether, butylene glycol, dipropylene glycol and diethylene glycol alkyl ethers, for instance diethylene glycol monoethyl ether or monobutyl ether, or alternatively polyols, for instance glycerol. Polyethylene glycols and polypropylene glycols, and mixtures of all these compounds, may also be used as solvent.

The at least one common solvent may be present in the composition, if it is present, in an amount ranging from 1% to 40% by weight, such as from 5% to 30% by weight, relative to the total weight of the composition.

The pH of the composition as disclosed herein may generally range from about 3 to 12, for instance from about 5 to 11. The pH may be adjusted to the desired value by means of acidifying or basifying agents.

Non-limiting examples of acidifying agents that may be mentioned include mineral or organic acids, for instance hydrochloric acid, orthophosphoric acid, sulphuric acid, carboxylic acids, for instance acetic acid, tartaric acid, citric acid and lactic acid, and sulphonic acids.

Non-limiting examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (E):

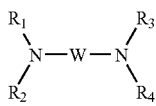

wherein W is chosen from propylene residues optionally substituted with an entity chosen from hydroxyl groups and $C_1$-$C_6$ alkyl radicals; $R_1$, $R_2$, $R_3$ and $R_4$, which may be identical or different, may be chosen from hydrogen atoms, $C_1$-$C_6$ alkyls, and $C_1$-$C_6$ hydroxyalkyl radicals.

According to one aspect of the present disclosure, the composition may comprise, in addition to the at least one fluorescent dye, at least one non-fluorescent direct dye of nonionic, cationic or anionic nature, which may be chosen, for example, from nitrobenzene dyes.

For example, non-limiting mention may be made of the following red and orange non-fluorescent nitrobenzene direct dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The composition in accordance with the present disclosure may also comprise, in addition to, or instead of these nitrobenzene dyes, at least one additional direct dyes chosen from yellow, green-yellow, blue and violet nitrobenzene dyes, azo dyes, anthraquinone dyes, naphthoquinone dyes, benzoquinone dyes, phenothiazine dyes, indigoid dyes, xanthene dyes, phenanthridine dyes and phthalocyanin dyes, triarylmethane-based dyes, and mixtures thereof.

The at least one additional direct dye may be for example, chosen from basic dyes, among which, non-limiting mention may be made of the dyes known in the Color Index, 3rd edition, under the names "Basic Brown 16," "Basic Brown 17," "Basic Yellow 57," "Basic Red 76," "Basic Violet 10," "Basic Blue 26" and "Basic Blue 99," and acidic direct dyes, among which non-limiting mention may be made of the dyes known in the Color Index, 3rd edition, under the names "Acid Orange 7," "Acid Orange 24," "Acid Yellow 36," Acid Red 33," "Acid Red 184," "Acid Black 2," "Acid Violet 43," and "Acid Blue 62," or alternatively cationic direct dyes such as those described in patent applications WO 95/01772, WO 95/15144 and EP-A-0 714 954, the content of which is incorporated herein by reference.

Among the additional yellow and green-yellow nitrobenzene direct dyes that may be used, non-limiting mention may be made, for example, of the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue and violet nitrobenzene direct dyes that may be used, non-limiting mention may be made, for example, of the compounds chosen from:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitroparaphenylenediamines of formula:

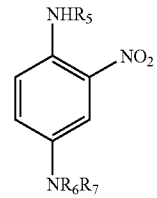

wherein:
$R_6$ may be chosen from $C_1$-$C_4$ alkyl radicals and β-hydroxyethyl, β-hydroxypropyl and γ-hydroxypropyl radicals;
$R_5$ and $R_7$, which may be identical or different, may be chosen from β-hydroxyethyl, β-hydroxypropyl, γ-hydroxypropyl and β,γ-dihydroxypropyl radicals, provided that at least one of the radicals $R_6$, $R_7$ or $R_5$ comprise a γ-hydroxypropyl radical and $R_6$ and $R_7$ do not simultaneously comprise a β-hydroxyethyl radical when $R_6$ is a γ-hydroxypropyl radical, such as those described in FR 2,692,572.

When they are present, the at least one non-fluorescent direct dye may be present in an amount ranging from about 0.0005% to about 12% by weight, relative to the total weight of the composition, for instance from about 0.005% to about 6% by weight, relative to the total weight of the composition.

When it is intended for oxidation dyeing, the composition in accordance with the present disclosure comprises, in addition to the at least one fluorescent dye, at least one oxidation base chosen from the oxidation bases conventionally used for oxidation dyeing, and among which non-limiting mention may be for example, of para-phenylene-diamines, bis(phenyl)alkylenediamines, para-aminophenols, ortho-aminophenols, heterocyclic bases, and the addition salts thereof with an acid or with an alkaline agent.

Among the para-phenylenediamines that may be used, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-O-acetylaminoethyloxy-para-phenylenediamine, N-(β-methoxyethyl)-para-phenylenediamine, 4'-aminophenyl-1-(3-hydroxy)pyrrolidine, and the addition salts thereof with an acid or with an alkaline agent.

For instance, among the para-phenylenediamines mentioned above, non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof with an acid or with an alkaline agent.

Among the bis(phenyl)alkylenediamines that may be used, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the addition salts thereof with an acid or with an alkaline agent.

Among the para-aminophenols that may be used, non-limiting mention may be made of, for example, para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the addition salts thereof with an acid or with an alkaline agent.

Among the ortho-aminophenols that may be used, non-limiting mention may be made of, for example, 2-aminophenol, 2-amino-5-methylphenol, 2-amino-6-methylphenol, 5-acetamido-2-aminophenol, and the addition salts thereof with an acid or with an alkaline agent.

Among the heterocyclic bases that may be used, non-limiting mention may be made, for example, of pyridine derivatives, pyrimidine derivatives and pyrazole derivatives, and the addition salts thereof with an acid or with an alkaline agent.

The at least one oxidation base, when used, may be present in an amount, for example, ranging from about 0.0005% to about 12% by weight, relative to the total weight of the composition, for instance from about 0.005% to about 6% by weight, relative to the total weight of the composition.

When it is intended for oxidation dyeing, the composition in accordance with the present disclosure may also comprise, in addition to the at least one fluorescent dye, at least one aminosilicone, and at least one oxidation base, at least one coupler that may modify or enrich with glints the shades obtained using the composition as disclosed herein.

The couplers that may be used in the composition in accordance with the present disclosure may be chosen from couplers conventionally used in oxidation dyeing, and among which non-limiting mention may be made of, for example, meta-phenylenediamines, meta-aminophenols, meta-diphenols and heterocyclic couplers, and the addition salts thereof with an acid or with an alkaline agent. For example, the at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and the addition salts thereof with an acid or with an alkaline agent.

The at least one coupler, when used in the composition, may be present in an amount for example, ranging from about 0.0001% to about 10% by weight, such as from about 0.005% to about 5% by weight, relative to the total weight of the composition.

In general, the addition salts with an acid that may be used in the context of the compositions as disclosed herein, i.e., with oxidation bases and couplers, may be chosen from, for example, hydrochlorides, hydrobromides, sulphates, citrates, succinates, tartrates, tosylates, benzenesulphonates, lactates and acetates. For example, the addition salts with an alkaline agent that may be used in the context of the compositions as disclosed herein may be chosen from the addition salts with alkali metals and alkaline-earth metals, with ammonia and with organic amines, including alkanolamines and the compounds of formula (E) described above.

The composition in accordance with the present disclosure may also comprise various conventionally used adjuvants, such as anionic, cationic, nonionic, amphoteric and zwitterionic surfactants and mixtures thereof, anionic, cationic, nonionic, amphoteric and zwitterionic polymers other than those of the composition disclosed herein, and mixtures thereof, mineral thickeners, antioxidants, penetrating agents, sequestering agents, fragrances, buffers, dispersants, conditioners, for instance cations, film-forming agents, ceramides, preserving agents, stabilizers and opacifiers.

Among the thickeners that may be used, non-limiting mention may be made of, for example, thickening systems based on associative polymers that are known to those skilled in the art, for instance, those of nonionic, anionic, cationic and amphoteric nature.

The at least one surfactant, when used in the composition, for example those of the nonionic, anionic and amphoteric type, may be present in an amount ranging from about 0.01% to about 30% by weight, relative to the total weight of the composition.

Needless to say, a person skilled in the art will take care to select any of the optional additional compounds discussed herein such that the advantageous properties intrinsically associated with the composition in accordance with the invention are not, or are not substantially, adversely affected by the envisaged addition.

The composition according to the present disclosure may be in various forms, such as in the form of liquids, shampoos, creams or gels, or in any other suitable form. According to one aspect of the present disclosure, the composition is in the form of a lightening dye shampoo and further comprises a cosmetically acceptable aqueous medium.

In the composition according to the present disclosure, when at least one oxidation base is used, optionally in the presence of at least one coupler, or when the at least one fluorescent dye is used in the context of a lightening direct dyeing, then the composition in accordance with the present disclosure may also comprise at least one oxidizing agent.

The at least one oxidizing agent may be chosen, for example, from hydrogen peroxide, urea peroxide, alkali metal bromates, persalts such as perborates and persulphates, and enzymes such as peroxidases and two-electron or four-electron oxidoreductases. For example, the at least one oxidizing agent may be chosen from hydrogen peroxide and enzymes.

One aspect of the present disclosure is also the method of use of a composition comprising, in a cosmetically acceptable medium, at least one fluorescent dye that is soluble in the medium, and at least one aminosilicone, for dyeing human keratin materials with a lightening effect. In the context of this aspect of the present disclosure, the at least one fluorescent dye may be chosen, for example, from those belonging to the following families: naphthalimides; cationic and non-cationic coumarins; xanthenodiquinolizines, such as sulphorhodamines; azaxanthenes; naphtholactams; azlactones; oxazines; thiazines; dioxazines; monocationic and polycationic fluorescent dyes of azo, azomethine and methine type, alone or as mixtures.

For example, non-limiting mention may be made of fluorescent dyes of formulae F1, F2 and F3, detailed above.

It is similarly possible to use the compounds of structure (F4):

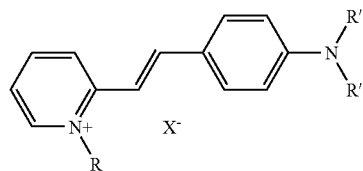

wherein R is chosen from methyl and ethyl radicals; R' is chosen from methyl radicals, and X⁻ is chosen from anions, such as chloride, iodide, sulphate, methosulphate, acetate and perchlorate. An example of a compound of this type that may be mentioned is the Photosensitizing Dye NK-557 sold by the company Ubichem, wherein R is chosen from ethyl radicals, R' is chosen from methyl radicals, and X⁻ is chosen from iodide.

Everything that has been described previously regarding the natures and contents of the various additives present in the composition remains valid and will not be repeated in this section.

According to the present disclosure, the term "human keratin materials" means the skin, the hair, the nails, the eyelashes and the eyebrows, and for example, dark skin and artificially colored and pigmented hair.

For the purposes of the present disclosure, the term "dark skin" means a skin whose lightness L* measured in the CIEL L*a*b* system is less than or equal to 45, for instance, less than or equal to 40, given that L*=0 is equivalent to black and L*=100 is equivalent to white. The skin types corresponding to this lightness include African skin, afro-American skin, hispano-American skin, Indian skin and North African skin.

As used herein, the expression "artificially dyed or pigmented hair" means hair with a tone height of less than or equal to 6, i.e., dark blond, for example, less than or equal to 4, i.e., chestnut-brown.

The lightening of the hair is evaluated by the "tone height", which characterizes the degree or level of lightening. The notion of "tone" is based on the classification of the natural shades, one tone separating each shade from the shade immediately following or preceding it. This definition and the classification of the natural shades are known to hairstyling professionals and are published in the book *Sciences des traitements capillaires [Hair treatment sciences]* by Charles Zviak, 1988, published by Masson, pp. 215 and 278. The tone heights range from 1 (black) to 10 (light blond), wherein one unit corresponds to one tone; the higher the figure, the lighter the shade.

Another aspect of the present disclosure thus concerns a process for dyeing human keratin fibers with a lightening effect, which comprises performing the following steps:
  a) the composition according to the present disclosure is applied to the keratin fibers, for a time that is sufficient to develop the desired coloration and lightening,
  b) the fibers are optionally rinsed,
  c) the fibers are optionally washed with shampoo and rinsed,
  d) the fibers are dried or are left to dry.

Another aspect of the present disclosure is also a process for coloring dark skin with a lightening effect, wherein the composition described herein is applied to the skin and the skin is then dried or is left to dry. For example, this composition may not have to comprise any oxidation base or coupler and may not need to be used in the presence of an oxidizing agent.

Everything that has been described previously regarding the various constituent components of the composition remains valid, and reference may be made thereto.

For further example, the processes according to the present disclosure are suitable for treating human keratin fibers, such as artificially colored or pigmented hair, or alternatively dark skin. The fibers that may be treated with the process according to the present disclosure, for instance, may have a tone height of less than or equal to 6, i.e., dark blond, such as less than or equal to 4, i.e., chestnut-brown.

Furthermore, a dark skin capable of being treated in accordance with the present disclosure has a lightness L*, measured in the CIEL L*a*b* system, of less than or equal to 45, such as less than or equal to 40.

According to a first aspect of the present disclosure, the process of dyeing fibers with a lightening effect is performed with a composition that does not comprise any oxidation dyes or coupler and in the absence of oxidizing agent.

According to a second aspect of the present disclosure, the process of dyeing fibers with a lightening effect is performed with a composition that does not comprise any oxidation dyes or coupler, but in the presence of at least one oxidizing agent.

According to a first variant of these dyeing processes in accordance with the present disclosure, at least one composition as defined above is applied to the fibers, for instance the hair, for a time that is sufficient to develop the desired coloration and lightening, after which the fibers are rinsed, optionally washed with shampoo, rinsed again and dried.

According to a second variant of these dyeing processes in accordance with the present disclosure, at least one composition as defined above is applied to the fibers, such as the hair, without final rinsing.

According to a third dyeing process variant in accordance with the present disclosure, the dyeing process comprises a preliminary step that comprises separately storing, at least one composition according to the present disclosure optionally comprising at least one oxidation base and/or one coupler, and, separately storing at least one composition comprising, in a cosmetically acceptable medium, at least one oxidizing agent, and then in mixing the separately stored compositions together at the time of use, after which this mixture is applied to the keratin fibers, such as the hair, for a time that is sufficient to develop the desired coloration, after which the fibers are rinsed, optionally washed with shampoo, rinsed again and dried.

The time required to develop the coloration and to obtain the lightening effect on the fibers, especially the hair, is about 5 to 60 minutes and more particularly about 5 to 40 minutes.

The temperature required to develop the coloration and to obtain the lightening effect generally ranges from about 15° C. to about 80° C., for instance, from about 15° C. to about 40° C., for example, about room temperature.

Yet another aspect of the present disclosure is a multi-compartment device or kit for dyeing keratin fibers, such as the hair, with a lightening effect, comprising at least one compartment containing a composition according to the present disclosure, and at least one other compartment containing a composition comprising at least one oxidizing agent. This device may be equipped with a means for applying the desired mixture to the fibers, such as the devices described in patent FR 2,586,913.

It should be noted that the composition according to the present disclosure, if it is used to treat keratin fibers, for example such as chestnut-brown hair, the following reflectance results are possible: If the reflectance of the hair is measured when it is irradiated with visible light in the wavelength range from about 400 to about 700 nanometres, and if the curves of reflectance as a function of the wavelength are compared for hair treated with the composition of the present disclosure and untreated hair, it is found that the reflectance curve corresponding to the treated hair, in a wavelength range from about 500 to about 700 nanometres, is higher than that corresponding to the untreated hair. As used herein, the term "higher than" means a difference of at least 0.05%, such as at least 0.1% of reflectance. This means that, in the wavelength range from about 500 to about 700 nanometres, for instance from about 540 to about 700 nanometres, there is at least one range in which the reflectance curve corresponding to the treated hair is higher than the reflectance curve corresponding to the untreated hair. However, it is noted that there may be, within the wavelength range from about 500 to about 700 nanometres, such as from about 540 to about 700 nanometres, at least one range of the reflectance curve corresponding to the treated fibers may be either superimposable on, or lower than, the reflectance curve corresponding to the untreated fibers.

For example, the wavelength at which the difference is maximal between the reflectance curve for the treated hair and that for the untreated hair may be in the wavelength range from about 500 to about 650 nanometres, such as in the wavelength range from about 550 to about 620 nanometres.

In addition, for instance, the composition according to the present disclosure is capable of lightening the hair and the skin in a shade which, measured in the CIEL L*a*b* system, has a variable b* of greater than or equal to 6, with a ratio of b*/(absolute value of a*) greater than 1.2, according to the selection test described below.

Selection Test

The composition as disclosed herein is applied to chestnut-brown keratin fibers, such as the hair, at a rate of 10 grams of composition per 1 gram of chestnut-brown fibers. The composition is spread on so as to cover all of the fibers. The composition is left to act for 20 minutes at room temperature, ranging from about 20° C. to 25° C. The fibers are then rinsed with water and then washed with a shampoo based on lauryl ether sulphate. They are then dried. The spectrocolorimetric characteristics of the fibers are then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

EXAMPLES

Fluorescent Compound

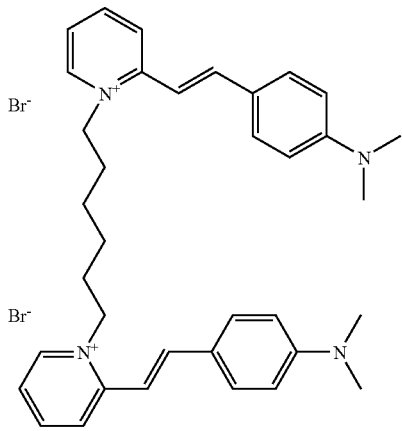

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4 \cdot 2Br$.

| Compositions | | | |
|---|---|---|---|
| Composition | 1 | 2 | 3 |
| Fluorescent compound | 1% | 1% | 1% |
| DC2939 (sold by Dow Corning) | 0.2% | — | — |
| DC28299 (sold by Dow Corning) | — | 0.2% | — |
| Fluid WR 1300 (sold by Wacker) | — | — | 0.2% |
| Distilled water | qs. 100% | qs 100% | qs. 100% |

Coloration

The composition was applied to a lock of natural chestnut-brown hair (tone height 4) and left on the hair for 20 minutes.

The locks were then rinsed and dried under a hood for 30 minutes.

A marked lightening effect was observed on each of the treated locks.

What is claimed is:

1. A cosmetic composition comprising, in a cosmetically acceptable medium, at least one fluorescent dye that is soluble in the medium and at least one aminosilicone, wherein the at least one fluorescent dye is chosen from formula (F3):

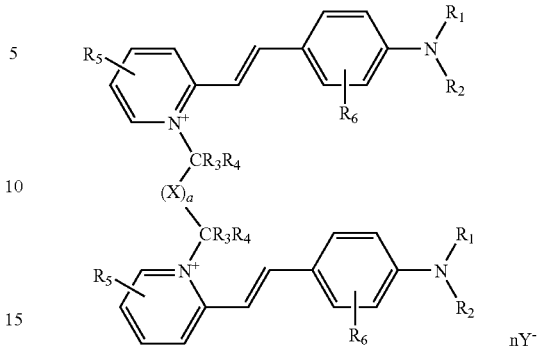

wherein:
$R_1$ and $R_2$, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
aryl and arylalkyl radicals, wherein the aryl group comprises 6 carbon atoms and the alkyl radical comprises from 1 to 4 carbon atoms; the aryl radical is optionally substituted with at least one radical chosen from linear and branched alkyl radicals comprising from 1 to 4 carbon atoms optionally interrupted with at least one entity chosen from hetero atoms and groups comprising at least one hetero atom, and optionally substituted with at least one entity chosen from hetero atoms, groups comprising at least one hetero atom, and halogen atoms;
$R_1$ and $R_2$ may optionally be linked so as to form a heterocycle with the nitrogen atom and may further comprise at least one hetero atom, wherein the heterocycle is optionally substituted with at least one radical chosen from linear and branched alkyl radicals, optionally interrupted with at least one entity chosen from hetero atoms and groups comprising at least one hetero atom, and optionally substituted with at least one entity chosen from hetero atoms, groups comprising at least one hetero atom, and halogen atoms;
$R_1$ or $R_2$ may also optionally be included in a heterocycle comprising the nitrogen atom and one of the carbon atoms of the phenyl group comprising the nitrogen atom;
$R_3$ and $R_4$, which may be identical or different, are chosen from hydrogen atoms and alkyl radicals comprising from 1 to 4 carbon atoms;
$R_5$, which may be identical or different, are chosen from hydrogen atoms, halogen atoms, and linear and branched alkyl radicals comprising from 1 to 4 carbon atoms, optionally interrupted with at least one hetero atom;
$R_6$, which may be identical or different, are chosen from hydrogen atoms; halogen atoms; and linear and branched alkyl radicals comprising from 1 to 4 carbon atoms, optionally interrupted with at least one entity chosen from hetero atoms and groups comprising at least one hetero atoms, and optionally substituted with at least one entity chosen from hetero atoms, groups comprising at least one hetero atom, and halogen atoms;

X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;

5- and 6-membered heterocyclic radicals optionally substituted with at least one radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;

dicarbonyl radicals;
the group X optionally comprises at least one cationic charge;

a is equal to 0 or 1;

Y⁻, which may be identical or different, is chosen from organic and mineral anions; and n is an integer ranging from 2 to the number of cationic charges present in the fluorescent dye.

2. The cosmetic composition according to claim 1, wherein $R_1$ and $R_2$, which may be identical or different, are chosen from linear and branched alkyl radicals comprising from 1 to 4 carbon atoms optionally interrupted with at least one entity chosen from hetero atoms and groups comprising at least one hetero atom, and optionally substituted with at least one entity chosen from hetero atoms, groups comprising at least one hetero atom, and halogen atoms.

3. The cosmetic composition according to claim 1, wherein the heterocycle formed by $R_1$ and $R_2$ with the nitrogen atom is substituted with at least one radical chosen from linear and branched alkyl radicals comprising from 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms.

4. The cosmetic composition according to claim 1, wherein the at least one fluorescent dye is present in an amount ranging from about 0.01% to about 20% by weight, relative to the total weight of the cosmetic composition.

5. The cosmetic composition according to claim 4, wherein the at least one fluorescent dye is present in an amount ranging from about 0.05% to about 10% by weight, relative to the total weight of the cosmetic composition.

6. The cosmetic composition according to claim 5, wherein the at least one fluorescent dye is present in an amount ranging from about 0.1% to about 5% by weight, relative to the total weight of the cosmetic composition.

7. The cosmetic composition according to claim 1, wherein the at least one aminosilicone is chosen from those of formula (A):

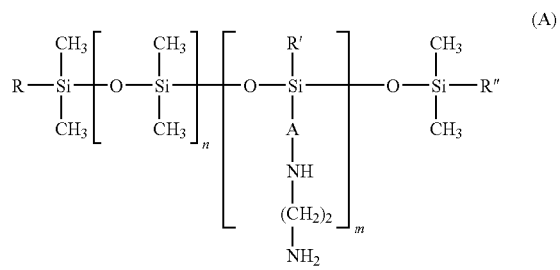

wherein R, R' and R", which may be identical or different, are chosen from $C_1$-$C_4$ alkyl radicals; $C_1$-$C_4$ alkoxy radicals; and OH; A is chosen from linear and branched $C_3$-$C_8$ alkylene radicals; and m and n are integers such that the sum of which ranges from 1 to 2000.

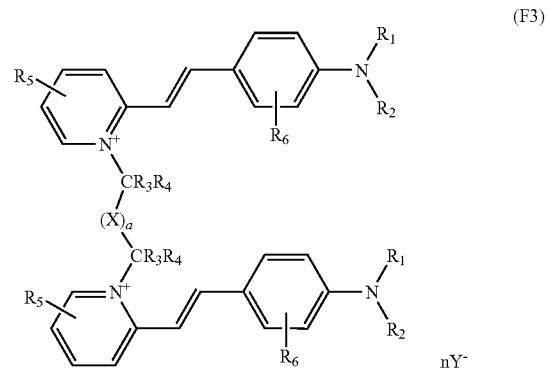

8. The cosmetic composition according to claim 7, wherein R, R' and R", which may be identical or different, are chosen from $CH_3$; methoxy; and OH.

9. The cosmetic composition according to claim 1, wherein the at least one aminosilicone is present in an amount ranging from about 0.01% to about 20% by weight, relative to the weight of the cosmetic composition.

10. The cosmetic composition according to claim 9, wherein the at least one aminosilicone is present in an amount ranging from about 0.1% to about 10% by weight, relative to the weight of the cosmetic composition.

11. The cosmetic composition according to claim 1, in the form of a lightening dyeing shampoo.

12. A multi-compartment kit for dyeing and lightening human keratin materials, comprising at least one compartment comprising a cosmetic composition comprising, in a cosmetically acceptable medium, at least one fluorescent dye that is soluble in the medium and at least one aminosilicone;

wherein the at least one fluorescent dye is chosen from formula (F3):

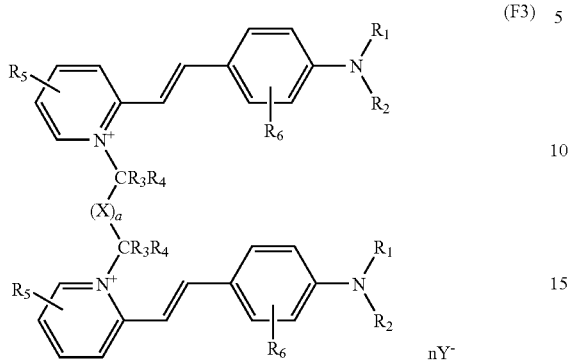

wherein:
R$_1$ and R$_2$, which may be identical or different, are chosen from:
hydrogen atoms;
linear and branched alkyl radicals comprising from 1 to 10 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
aryl and arylalkyl radicals, wherein the aryl group comprises 6 carbon atoms and the alkyl radical comprises from 1 to 4 carbon atoms; the aryl radical is optionally substituted with at least one radical chosen from linear and branched alkyl radicals comprising from 1 to 4 carbon atoms optionally interrupted with at least one entity chosen from hetero atoms and groups comprising at least one hetero atom, and optionally substituted with at least one entity chosen from hetero atoms, groups comprising at least one hetero atom, and halogen atoms:
R$_1$ and R$_2$ may optionally be linked so as to form a heterocycle with the nitrogen atom and may further comprise at least one hetero atom, wherein the heterocycle is optionally substituted with at least one radical chosen from linear and branched alkyl radicals, optionally interrupted with at least one entity chosen from hetero atoms and groups comprising at least one hetero atom, and optionally substituted with at least one entity chosen from hetero atoms, groups comprising at least one hetero atom, and halogen atoms;
R$_1$ or R$_2$ may also optionally be included in a heterocycle comprising the nitrogen atom and one of the carbon atoms of the phenyl group comprising the nitrogen atom;
R$_3$ and R$_4$, which may be identical or different, are chosen from hydrogen atoms and alkyl radicals comprising from 1 to 4 carbon atoms;
R$_5$, which may be identical or different, are chosen from hydrogen atoms, halogen atoms, and linear and branched alkyl radicals comprising from 1 to 4 carbon atoms, optionally interrupted with at least one hetero atom;
R$_6$, which may be identical or different, are chosen from hydrogen atoms; halogen atoms; and linear and branched alkyl radicals comprising from 1 to 4 carbon atoms, optionally interrupted with at least one entity chosen from hetero atoms and groups comprising at least one hetero atoms, and optionally substituted with at least one entity chosen from hetero atoms, groups comprising at least one hetero atom, and halogen atoms;
X is chosen from:
linear and branched alkyl radicals comprising from 1 to 14 carbon atoms and alkenyl radicals comprising from 2 to 14 carbon atoms, optionally interrupted with at least one entity chosen from hetero atoms and groups comprising at least one hetero atom, and optionally substituted with at least one entity chosen from hetero atoms, groups comprising at least one hetero atom, and halogen atoms;
5- and 6-membered heterocyclic radicals optionally substituted with at least one radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one hetero atom and/or group comprising at least one hetero atom;
dicarbonyl radicals;
the group X optionally comprises at least one cationic charge;
a is equal to 0 or 1;
Y$^-$, which may be identical or different, is chosen from organic and mineral anions; and
n is an integer ranging from 2 to the number of cationic charges present in the fluorescent dye;
and at least one other compartment comprising a composition comprising at least one oxidizing agent.

13. The multi-compartment kit according to claim 12, wherein the human keratin materials are chosen from artificially and naturally colored keratin fibers, and dark skin.

* * * * *